(12) United States Patent
Lee et al.

(10) Patent No.: US 8,455,014 B2
(45) Date of Patent: Jun. 4, 2013

(54) **COMPOSITION COMPRISING *TRACHELOSPERMI CAULIS* AND *PYROLA JAPONICA* EXTRACTS FOR THE TREATMENT AND PREVENTION OF INFLAMMATORY DISEASES**

(75) Inventors: Jeong Min Lee, Gunpo-si (KR); Chul Gyu Ha, Gyeonggi-do (KR); Mu Hong Lee, Gyeonggi-do (KR); Seung Ha Lee, Seongnam-si (KR); Jae Yoon Leem, Iksan-si (KR); Wahn Soo Choi, Seoul (KR); Sung Hoon Jun, Cheongju-si (KR); Jee Hun Park, Seoul (KR)

(73) Assignee: Sinil Pharmaceutical Co., Ltd., Chungcheongbuk-do (KR)

( * ) Notice: Subject to any disclaimer, the term of this patent is extended or adjusted under 35 U.S.C. 154(b) by 536 days.

(21) Appl. No.: 12/524,122

(22) PCT Filed: Dec. 20, 2007

(86) PCT No.: PCT/KR2007/006683
§ 371 (c)(1),
(2), (4) Date: Jul. 22, 2009

(87) PCT Pub. No.: WO2008/091064
PCT Pub. Date: Jul. 31, 2008

(65) Prior Publication Data
US 2009/0317495 A1  Dec. 24, 2009

(30) Foreign Application Priority Data
Jan. 24, 2007  (KR) .......................... 10-2007-0007616

(51) Int. Cl.
*A61K 36/00* (2006.01)
(52) U.S. Cl.
USPC ........................................................ 424/725

(58) Field of Classification Search
None
See application file for complete search history.

(56) References Cited

U.S. PATENT DOCUMENTS

| 2006/0018867 | A1 * | 1/2006 | Kawasaki et al. | ........ 424/70.122 |
| 2006/0177472 | A1 * | 8/2006 | Tomioka | ...................... 424/405 |

FOREIGN PATENT DOCUMENTS

| CN | 1813965 | * | 8/2006 |
| CN | 1814066 | * | 8/2006 |
| CN | 1919856 | * | 2/2007 |
| JP | 03190809 | * | 8/1991 |
| JP | 08-301779 | A | 11/1996 |
| JP | 08301779 | * | 11/1996 |
| JP | 2005194246 | * | 7/2005 |

OTHER PUBLICATIONS

Wi, Rachel W. et al.: "Anti-inflammatory activity of Chinese medicinal vine plants", *Journal of Ethnopharmacology*, vol. 85, Issue 1, Mar. 2003, Abstract only.

* cited by examiner

*Primary Examiner* — Christopher R Tate
(74) *Attorney, Agent, or Firm* — Frommer Lawrence & Haug LLP; Ronald R Santucci (57) ABSTRACT

The present invention relates to a pharmaceutical composition for the prevention and treatment of inflammatory diseases comprising a mixture of herbal extracts of *Trachelospermi caulis* and *Pyrola japonica* as active ingredients. More particularly, the pharmaceutical composition of the present invention comprises a mixture of herbal extracts of *Trachelospermi caulis* and *Pyrola japonica* in a predetermined range thereby exhibiting superior on therapeutic effects for the treatment of pains, acute inflammation, secretion of enzymes associated with factors inducing inflammation, and production of NO, iNOS, etc., as compared to those prepared from single herbal drugs, thus being useful in the prevention and treatment of inflammatory diseases such as arthritis.

8 Claims, 5 Drawing Sheets

(*MHD denotes mixed herbal drug.)

FIG. 5

(*MHD denotes mixed herbal drug)

FIG. 6

(*MHD denotes mixed herbal drug.)

COMPOSITION COMPRISING *TRACHELOSPERMI CAULIS* AND *PYROLA JAPONICA* EXTRACTS FOR THE TREATMENT AND PREVENTION OF INFLAMMATORY DISEASES

This application is a 371 of PCT/KR2007/006683 filed on Dec. 20, 2007 published on Jul. 31, 2008 under publication number WO 2008/091064 A and claims priority benefits of Korean Patent Application No. 10-2007-0007616 filed Jan. 24, 2007, the entire contents of which are hereby incorporated by reference.

BACKGROUND OF THE INVENTION

1. Field of the Invention

The present invention relates to a pharmaceutical composition for the prevention and treatment of inflammatory diseases comprising a mixture of herbal extracts of *Trachelospermi caulis* and *Pyrola japonica* as active ingredients. More particularly, the pharmaceutical composition of the present invention comprises a mixture of herbal extracts of *Trachelospermi caulis* and *Pyrola japonica* mixed in a predetermined ratio thereby exhibiting superior inhibitory effects on pains, acute inflammation, secretion of enzymes associated with factors inducing inflammation, and production of NO, iNOS, etc., as compared to those prepared from single herbal drugs, thus being useful in the prevention and treatment of inflammatory diseases such as arthritis.

2. Background Art

Arthritis is a collectively term for a disease associated with inflammatory changes which occur within a joint region due to bacterial infection or external injuries. Arthritis is largely classified into two: acute arthritis and chronic arthritis.

Acute arthritis is further divided as follows. (1) Serous arthritis—generally caused by external injuries, but may occur due to unknown reasons. It generally occurs in one joint. (2) Serofibrinous arthritis—this occurs with the acute rheumatoid arthritis, and a turbid effusion is gathered in the articular cavity. This may cause dyscinesia even after inflammation is deteriorated due to the generation of pseudomembrane. (3) Supprative arthritis—multiple arthritis occurs in the open wounds of a joint or contagious diseases such as gonorrhea, typhoid, scarlatinal, and septicemic. Young infants of 1-2 months old may develop abarticulation due to the uncurable severe damage on bones. Adults often develop periosteomyelitis which causes rupture and allows the pus to be flowed into joints, so called secondary supprative arthritis.

Chronic arthritis can be further divided as follows.

(1) Specific type of inflammation—generally refers to a gouty arthritis caused by tuberculous arthritis or syphilitic arthritis or metabolic disorder in uric acid commonly occurring in middle aged men.

(2) Multiple arthritis—chronic rheumatoid arthritis is most common. This may be transited from the acute serous arthritis, may occur as a polyarthritis in the course of pneumonia, syphilis, and gonorrhea, or may be a kind of septicemia. In addition, Still's disease also belongs to this category.

(3) Arthritis deformans—generally caused by degenerative aging process or external injuries.

(4) Hemophiliac arthritis—caused by bleeding in the joints in a hemophiliac patient.

Degenerative arthritis is also called as 'bone arthritis'. It is a local arthritis resulted from the change in degeneration of joint cartilage, and occurs mainly in middle aged or senior people. The main cause of the local arthritis appears to be aging because it occurs in about 85% of people of 55-65 years of age. It is reported that it occurs more frequently in women than in men, and is also more severe in women than in men. In addition, it occurs two times more frequently in obese people than in normal healthy people, especially in leg cartilages where body weights are loaded, for example, hip joints, knee joints, ankle joints, etc. It also occurs in end joints of hands. The arthritic pains usually come after excessive movements of joints or at evenings, and the symptoms are improved after rest.

The initial stiffness felt by a subject in the morning can be easily removed after body movement of for about 5-10 min. In case when the symptom is severe or progressed to some extent, and thus joints make a cracking noise during movement, and in a more severe case, joint movement is much restricted. Sometimes, joints which endure body weights, in particular knee joints, cannot be used at all but, after a while, the symptom is often recovered spontaneously without any special treatment. Generally, in about 35% of women and 15% of men who are aged 60 or older, the symptoms associated with degenerative arthritis are observed. The best therapeutic treatment to improve the symptoms is to do exercises or swim regularly to the extent suitable for each person, and an auxiliary exercise equipment may be used to assist the exercise. Examples of drugs to treat the symptoms are an anti-inflammatory and analgesic agent, an adrenocortical hormone agent, a cartilage protection agent, a surgery to inject a lubricant inside a joint, and the like. Many pharmaceutical drugs have been developed to be used for the treatment of the above-mentioned various kinds of inflammatory diseases represented by arthritis.

The present invention relates to a pharmaceutical composition comprising herbal extracts thus eliminating the risk of adverse effects often raised in synthetic drugs. In fact, the toxicity test for a single administration of a herbal drug comprising the herbal composition of the present invention confirmed its safety.

The herbal composition of the present invention comprises extracts of *Trachelospermi caulis* and *Pyrola japonica*. *Trachelospermi caulis* is also called as *Trachelospermum asiaticum var. intermedium Nakai*, and climbing stems and branches of *Trachelospermum sdisyivum var, intermedium nakai* or *Apocyanaceae*. It grows as high as 5 m. Its petals are branched deep inside into five. White flowers of a pinwheel shape bloom in May-June and emits a good scent. It will bear fruits around September-November, where the two long fruits remind of a Chinese character representing a person, and they often form a round circle showing the shape of a bracelet. In fact, *Trachelospermi caulis* grows in the seashore, hillside or a barren tract in the Southern part of Korea, more specifically, on the rocks, walls, or grows creepers onto other trees or plants. In areas where *Trachelospermi caulis* is abundant, it is possible that other kinds of grasses may not grow but only the place may be clothed with *Trachelospermi caulis*. According to the 'Dictionary of Oriental Medicine' published by North Korea, *Trachelospermi caulis* is the one which dried the stems and leaves of *Trachelospermum asiaticum var. intermedium Nakai*. It has a bitter taste and is cold in its property from the viewpoint of oriental medicine. It acts on spasm on heart meridian, liver meridian, and renal meridian. It also eliminates wind-dampness blended as a pathogenic factor and promotes smooth interconnection of meridian system. Besides, it is useful to treat paralytic syndrome, cramps of limbs, lumbago, arthritic pains, tonsillitis, and rashes.

The active ingredients of *Trachelospermi caulis* are arctiin, arctigenin, tracheloside, matairesinoside, cymarose, etc.

They are known to have vasodilating and hypotensive activities (Herb Medicinal Phamacology, LIM, Jongpil, p. 155-156 (2003)).

*Pyrola japonica* is an evergreen perennial herb that belongs to *Pyrola Klenze ex Alefeld*. Yellowish white or white flower blooms at the end of a flower stem as a raceme between June and July, its fruits ripen as capsules in August. Its leaves and stems are used as a hemostatic agent and an antidote. It contains arbutin and methylarbutin in the amount of about 1% as active ingredients, and also comprises homoarbutin, quercetin, ursollic acid, oleanoic acid, etc. It is generally known useful for the treatment of high blood pressure and arthritic pains [The Encyclopedia of Chinese Crude Drug, J. H. Park, p. 139-140 (2002)].

However, there has been no study done yet to elucidate the efficacies of a pharmaceutical drug comprising mixed herbal extracts. Further, the old herbal encyclopedia such as Donguibogam, Hyangyakjipsungbang, Gwangjebigeup or other related references only briefly mention the efficacies of these herbal drugs from the viewpoint of oriental medicine and a method of preparing a decoction. In addition, there has been no report on the prescription for preparing a decoction from a mixed herbal drug. In fact, there has been no report on the efficacies of the active ingredients mentioned above extracted using the above method. Further, there has been no teaching on preclinical trial using an animal model or pharmaceutical efficacies such as anti-inflammatory and pain-releasing and analgesic effects.

The information disclosed in this Background of the Invention section is only for enhancement of understanding the background of the invention and should not be taken as an acknowledgement or any form of suggestion that this information forms the prior art that is already known to a person skilled in the art.

SUMMARY OF THE INVENTION

As a result of intensive research efforts to resolve the above-mentioned problems by providing more scientific and objective data and optimize the extraction efficiency and, the inventors of the present invention discovered a pharmaceutical composition comprising two herbal extracts of *Trachelospermi caulis* and *Pyrola japonica* which are mixed in a suitable weight ratio to exhibit superior effects to treat pains and acute inflammation.

Therefore, an objective of the present invention is to provide a pharmaceutical composition for the prevention and treatment of inflammatory diseases comprising a mixture of herbal extracts of *Trachelospermi caulis* and *Pyrola japonica* as active ingredients

BRIEF DESCRIPTION OF THE DRAWINGS

The above and other features of the present invention will be described with reference to certain exemplary embodiments thereof illustrated the attached drawings in which.

DETAILED DESCRIPTION

The present invention relates to a pharmaceutical drug for the prevention and treatment of inflammatory diseases comprising a mixture of herbal extracts of *Trachelospermi caulis* and *Pyrola japonica* as active ingredients.

The present invention can be further described in detail as follows.

The present invention relates to a pharmaceutical drug which comprises a mixture of herbal extracts of *Trachelospermi caulis* and *Pyrola japonica* in a predetermined range thereby exhibiting superior inhibitory effects on pains, acute inflammation, secretion of enzymes associated with factors inducing inflammation, and production of NO, iNOS, etc., as compared to those prepared from single herbal drugs, thus being useful in the prevention and treatment of inflammatory diseases such as arthritis.

The mixed herbal drug composition comprising extracts of *Trachelospermi caulis* and *Pyrola japonica* were extracted by using water or an aqueous alcohol solution by using a method shown below.

The herbal drugs of *Trachelospermi caulis* and *Pyrola japonica* are minced into small pieces and they are mixed in a weight ratio of 1:1-1:15, preferably 1:1-1:5, and then extracted after adding the mixture with 10-15 times in weight of water, alcohol or an aqueous alcohol solution relative to the total weight of the mixed herbal drug. The filtrate obtained from the above extraction undergoes layer separation and the resulting alcohol layer is concentrated under reduced pressure at 60-80° C. During the concentrating step, the resulting extract undergoes azeotropic concentration, is lysophilized and is finally produced in the form of a powdered extract.

The extraction method of the present invention is described in more detail as follows.

The original herb drugs of *Trachelospermi caulis* and *Pyrola japonica* are mixed in a weight ratio of 1:1-1:15, preferably 1:1-1:5, added with water, alcohol, or an aqueous alcohol solution, undergoes an extraction 2-5 times for 2-3 hours of unit period of extraction. The resultant is slowly cooled down at room temperature, and separated from the residue by filtration via centrifugation. The resulting residue is then added with 10-15 times in weight of water, alcohol or an aqueous alcohol solution, relative to the total weight of the mixed herbal drug, heated, reextracted, filtrated, combined with the previous filtrate and then refiltrated. The reextraction performed by adding water, alcohol or an aqueous alcohol solution to the residue followed by filtration can increase extraction efficiency. Here, if the amount of water, alcohol or an aqueous alcohol solution is less than 10 times of the total weight of the mixed herbal drug, it will reduce solubility of the resulting extract thereby decreasing extraction efficiency. Meanwhile, if the amount of water, alcohol or an aqueous alcohol solution exceeds 15 times of the total weight of the mixed herbal drug, it will require an increased amount of alcohol to be used and also a longer time for concentration under reduced pressure thus being uneconomical and causing problems in handling.

As for the alcohol of the present invention, both aliphatic and aromatic alcohols may be used, preferably aliphatic alcohol, more preferably a $C_1$-$C_6$ low grade alcohol.

Further, an analysis on the extraction efficiency for each step showed that the yield by performing a reextraction in addition to the first extraction enabled to obtain about 80-90% of the total extract, although performing additional extractions of more than two reextractions did not increase the yield much thus being uneconomical.

As mentioned above, the extracts obtained by extracting with water, alcohol or an aqueous solution, are filtrated, concentrated, and then unnecessary proteins, polysaccharides, and fatty acids contained in the filtrate as impurities are purified. In the present invention, the impurities were removed by performing layer separation for the filtrate 2-5 times by using the same amount of an aqueous alcohol solution as a solvent and obtaining a solvent fraction therefrom.

It is preferable that the above alcohol is a $C_1$-$C_6$ alcohol, more preferably 30% ethanol. If the amount of the low grade aqueous alcohol is less than that of the filtrate it would prevent the process of a smooth layer separation due to the formation of granules by unnecessary components such as fatty acids, and is also not economical because the extracted contents of active ingredients are lowered.

The extraction liquid obtained after layer separation is concentrated at 60-80° C. under reduced pressure to remove the remaining solvent. Thus obtained concentrate is then added with an alcohol collected during the concentration under reduced pressure, added with the filtrate obtained after centrifugation at 500-1000 rpm and concentrated again under reduced pressure. Here, if the temperature for the concentration under reduced pressure is below 60 (C, the solvent cannot be removed completely. Meanwhile, if the temperature is above 80 (C, it would raise a problem in stability of the concentrate. If the concentrate is less than 500 rpm the separation of the concentrate from alcohol becomes difficult.

In contrast, if it exceeds 1,000 rpm it would raise a problem in stability of the concentrate.

Thus obtained concentrate is dried at 60-80 (C under 0.08-0.3 pa, and sterilized by passing through a 30-80 mesh sieve, and a mixture of *Trachelospermi caulis* extract and *Pyrola japonica* extract in the form of powder is finally obtained. Thus obtained mixed extract has superior therapeutic effects for the treatment of arthritis and pains as compared to that obtained from a single herbal drug and thus the mixed herbal drug comprising *Trachelospermi caulis* extract and *Pyrola japonica* extract will be useful for the prevention and treatment of inflammatory diseases.

The above herbal drugs used in the present invention were collected in Changsha city at Henan province of China. The mixed herbal drug contains arctiin, the major component of *Trachelospermi caulis*, in the amount of 0.5-4.3 wt %, and thus arctiin is used as a biomarker. The molecular formula of arctiin is C27H34O11.

The present invention also relates to a method for using a pharmaceutical drug comprising the above powdered extract as an active ingredient as a therapeutic agent for the treatment of degenerative arthritis and pains/inflammations. The effective physiologically active materials extracted from the pharmaceutical drug comprising *Trachelospermi caulis* and *Pyrola japonica* extracts were analyzed by using HPLC. The result revealed that arctiin and arctigenin are contained in the pharmaceutical drug, and arctiin and arctigenin have TNF-α inhibitory activity [Int Immunopharmacol. 2004 October; 4(10-11):1419-29, Arctigenin, a phenylpropanoid dibenzyl-butyrolactone lignan, inhibits MAP kinases and AP-1 activation via potent MKK inhibition: the role in TNF-α inhibition].

Arbutin, a major component of *Pyrola japonica*, is known to inhibit the activity of NF-κB, an inflammation inducing factor [J Dermatol Sci. 2003 May; 31(3):193-201, Down-regulation of NF-κB activation in human keratinocytes by melanogenic inhibitors].

For a therapeutic agent for the treatment of inflammatory disease according to the present invention, the intended therapeutic effect could be obtained when the content of arctiin, as a biomarker, is contained in the amount of 0.5-1.1 wt %. For example, if the content of arctiin is less than 0.5 wt %, the therapeutic effect for the treatment of arthritis, for example, is greatly deteriorated. There is no specific upper limit in the content of arctiin. However, the arctiin content exceeding the above range will not increase the intended therapeutic effect, and it is not also desirable in its technical and economical aspects. Therefore, it is preferable that the arctiin content be contained about 0.8-1.0 wt %.

Arctiin, the biomarker of the present invention, is an essential component of the therapeutic agent for the treatment of inflammatory diseases, and it can help a given therapeutic drug to exhibit an excellent drug efficacy by exerting a synergistic effect when it is contained a certain amount. Further, not only the above active ingredient but other ingredients of the therapeutic agent may also be involved in exerting the excellent therapeutic effect for the treatment of inflammatory diseases.

A method of preparing the *Trachelospermi caulis* extract of the present invention useful in the treatment of inflammatory diseases is described hereunder.

The complex pharmaceutical drug of the present invention comprising *Trachelospermi caulis* and *Pyrola japonica* extracts can be formulated by using a conventional method into tablets, capsules, injections, etc. If the combined amount of lactose, microcrystalline cellulose, magnesium stearate, etc., used as base materials for manufacturing tablets, is used along with the combined amount of *Trachelospermi caulis* and *Pyrola japonica* extracts in 1:1-1:15 weight ratio, the tablets manufactured thereof will have good therapeutic effects for the treatment of inflammatory diseases such as arthritis.

Herbal extracts themselves can be used as a therapeutic agent but they are in general combined with a carrier, a forming agent, a diluent, etc., and prepared into powder, granulates, capsules, or injections. The *Trachelospermi caulis* extract of the present invention has long been used as food as well as a drug. It has no special limit with regard to its dosage but it may vary depending on the rate of body absorption, body weight, age, sex, health conditions, diet of a patient, administration time, administration method, excretion rate, severeness of diseases, etc. In general, it is preferable to administer about 10-1000 mg of the mixed herbal extract per 1 kg of body weight, more preferably 50-500 mg.

Therefore, the composition comprising the active ingredient of the present invention should be manufactured considering its effective range, and a unit dosage preparation formulated thereof can be monitored of its administration, if necessary. Further, a specialized administration method may be used according to the decision and request of the patient or it may be administered a few times at regular intervals.

Reference will now be made in detail to the preferred embodiment of the present invention, examples of which are illustrated in the drawings attached hereinafter, wherein like reference numerals refer to like elements throughout. The embodiments are described below so as to explain the present invention by referring to the figures.

REFERENCE EXAMPLE 1

Preparation of *Trachelospermi caulis* Extract

*Trachelospermi caulis* was washed with sterile water, dried and then stirred after adding 30% ethanol in the amount of 5-8 times relative to the weight of the herbal drug, and heat-extracted twice at 2 hour unit. The resulting extract was cooled down to room temperature and underwent centrifugal filtration to remove impurities. The filtrates were combined and concentrated at 60-80° C. under reduced pressure. The concentrate was suspended in the ethanol recovered from the ethanol fraction, underwent centrifugal filtration at 1000 rpm, concentrated at 60° C. under reduced pressure, dried under the pressure of 0.08 pa, sterilized by passing through a 80 mesh sieve. The *Trachelospermi caulis* extract obtained as a result was analyzed by HPLC and was shown to contain 3.0-6.0 wt % of arctiin.

REFERENCE EXAMPLE 2

Preparation of *Pyrola japonica* Extract

*Pyrola japonica* was washed with sterile water, dried and then stirred after adding 30% ethanol in the amount of 5-8 times relative to the weight of the herbal drug, and heat-extracted twice at 2 hour unit. The resulting extract was cooled down to room temperature and performed centrifugal filtration to remove impurities. The filtrates were combined and concentrated at 60-80° C. under reduced pressure. The concentrate was suspended in the ethanol recovered from the ethanol fraction, underwent centrifugal filtration at 1000 rpm, concentrated at 60° C. under reduced pressure, dried under the pressure of 0.08 pa, sterilized by passing through a 80 mesh sieve. The *Pyrola japonica* extract obtained as a result was analyzed by HPLC and was shown to contain 0.1-1.0 wt % of arbutin.

REFERENCE EXAMPLE 3

Preparation of Mixed Herbal Extract

Equal amount of *Trachelospermi caulis* and *Pyrola japonica* were washed with sterile water, dried and then stirred after adding 30% ethanol in the amount of 5-8 times relative to the weight of the mixed herbal drug, and heat-extracted twice at 2 hour unit. The resulting extract was cooled down to room temperature and performed centrifugal filtration to remove impurities. The filtrates were combined and concentrated at 60-80° C. under reduced pressure. The concentrate was suspended in the ethanol recovered from the ethanol fraction, underwent centrifugal filtration at 1,000 rpm, concentrated at 60° C. under reduced pressure, dried under the pressure of 0.08 pa, sterilized by passing through a 80 mesh sieve. The mixed herbal drug composition obtained as a result was analyzed by HPLC and the result is shown in Table 1.

TABLE 1

| | |
|---|---|
| HPLC model: Jasco | |
| Autosampler: MODEL AS-2051 | |
| Pump: PU-2089 | |
| UV detector: 2075 | |
| HPLC conditions | |
| Mobile phase | MeOH 50% |
| Flow rate | 0.8 mL/min |

TABLE 1-continued

| | |
|---|---|
| HPLC model: Jasco | |
| Autosampler: MODEL AS-2051 | |
| Pump: PU-2089 | |
| UV detector: 2075 | |
| HPLC conditions | |
| Injection volume | 10 μL |
| Wavelength | 280 nm |
| column | C-18 COSMOSIL PACKED, 10 μm, 4.6*250 mm |

EXAMPLE 1

TPA-Induced Mice Ear Edema Assay

The effect of the mixed herbal extract obtained in the above reference example 3 on TPA-induced mouse ear edema was investigated. The weight of ear measured using a 6 mm punch was used as the ear weight. The result is shown in the following Table 2.

[Test Method]

Seven week old ICR mice were separated into each experimental group, orally administered with Joins® (SK Pharma Co., Ltd., Korea) at a concentration of 400 mg/kg and 200 mg/kg, *Trachelospermi caulis* extract at a concentration of 400 mg/kg and 200 mg/kg, respectively, *Pyrola japonica* extract at a concentration of 400 mg/kg and 200 mg/kg, respectively, and a mixed herbal extract of *Trachelospermi caulis* and *Pyrola japonica* at a concentration of 400 mg/kg, 200 mg/kg, 20 mg/kg, and 2 mg/kg, respectively. One hour after the oral administration, each mouse was treated on the right ear evenly with TPA (2.5 μg/20 μL), an inflammation inducing agent, after dissolving it in acetone, thereby inducing edema. During the experiment, an investigator fixed the subject tightly from the rear side and a second investigator stimulated an ear of each mouse with the edema-inducing material using a micropipette. Four hours later, ear edema was observed from mice in each experimental group. Mice were sacrificed via cervical dislocation for accurate observation and then the weight of edema was measured using a 6 mm punch.

TABLE 2

| Category | Dosage (mg/kg) | Average weight of edema (Mean ± S.D.) | Inhibitory rate (%) |
|---|---|---|---|
| Negative Control (saline solution) | 400 | 15.92 ± 0.79 | — |
| Positive Control (SK-Joins ®) | 400 | 8.62 ± 1.33 | 46 |
| | 200 | 11.69 ± 0.73 | 27 |
| *Trachelospermi caulis* extract | 400 | 7.58 ± 0.88 | 52 |
| | 200 | 8.23 ± 1.36 | 48 |
| *Pyrola japonica* extract | 400 | 11.52 ± 1.13 | 28 |
| | 200 | 11.74 ± 1.39 | 26 |
| Mixed herbal extract of *Trachelospermi caulis* and *Pyrola japonica* | 400 (1.0 wt % of arctiin content) | 7.41 ± 1.01 | 54 |
| | 200 (1.0 wt % of arctiin content) | 8.18 ± 1.32 | 49 |
| | 20 (1.0 wt % of arctiin content) | 11.73 ± 0.88 | 26 |
| | 2 (1.0 wt % of arctiin content) | 12.95 ± 1.73 | 18 |

As shown in the above Table 2, the mixed herbal extract of the present invention showed an excellent inhibitory effect against the TPA-induced ear edema. In particular, the highest edema inhibiting rate of 54% was observed when the concentration of the mixed herbal extract used was 400 mg/kg.

EXAMPLE 2

Arachidonic Acid-Induced Mice Ear Edema Assay

The effect of the mixed herbal extract obtained in the above reference example 3 on TPA-induced mouse ear edema was investigated. The result is shown in the following Tables 3 and 4.

[Test Method]

Seven week old ICR mice were separated into each experimental group, orally administered with Joins® (SK Pharma Co., Ltd., Korea) at a concentration of 400 mg/kg and 200 mg/kg, *Trachelospermi caulis* extract at a concentration of 400 mg/kg and 200 mg/kg, respectively, *Pyrola japonica* extract at a concentration of 400 mg/kg and 200 mg/kg, respectively, and a mixed herbal extract of *Trachelospermi caulis* and *Pyrola japonica* at a concentration of 400 mg/kg, 200 mg/kg, 20 mg/kg, and 2 mg/kg, respectively. One hour after the oral administration, each mouse was treated on the right ear with arachidonic acid (2 mg/20 μL), an inflammation inducing agent, after dissolving it in acetone, thereby inducing edema. During the experiment, an investigator fixed the subject tightly from the rear side and a second investigator stimulated an ear of each mouse with the edema-inducing material using a micropipette. One hour later, ear edema was observed from mice in each experimental group. Mice were sacrificed via cervical dislocation for accurate observation, the thickness of ear was measured using a micrometer and then the weight of edema was measured using a 6 mm punch.

TABLE 3

| Category | Dosage (mg/kg) | Average thickness of edema (Mean ± S.D.) | Inhibitory rate (%) |
|---|---|---|---|
| Negative Control | 400 | 0.55 ± 0.01 | — |
| Positive Control (SK-Joins ®) | 400 | 0.27 ± 0.02 | 52 |
|  | 200 | 0.3 ± 0.02 | 46 |
| *Trachelospermi caulis* extract | 400 | 0.22 ± 0.03 | 60 |
|  | 200 | 0.24 ± 0.05 | 56 |
| *Pyrola japonica* extract | 400 | 0.30 ± 0.05 | 46 |
|  | 200 | 0.35 ± 0.03 | 36 |
| Mixed herbal extract of *Trachelospermi caulis* and *Pyrola japonica* | 400 (1.0 wt % of arctiin content) | 0.20 ± 0.03 | 64 |
|  | 200 (1.0 wt % of arctiin content) | 0.21 ± 0.02 | 62 |
|  | 20 (1.0 wt % of arctiin content) | 0.40 ± 0.03 | 27 |
|  | 2 (1.0 wt % of arctiin content) | 0.48 ± 0.06 | 13 |

TABLE 4

| Category | Dosage (mg/kg) | Average weight of edema (Mean ± S.D.) | Inhibitory rate (%) |
|---|---|---|---|
| Negative Control (saline solution) | 400 | 15.2 ± 0.79 | — |
| Positive Control (SK-Joins ®) | 400 | 9.39 ± 1.33 | 38 |
|  | 200 | 10.91 ± 0.73 | 28 |
| *Trachelospermi caulis* extract | 400 | 7.66 ± 0.85 | 50 |
|  | 200 | 7.8 ± 0.89 | 49 |
| *Pyrola japonica* extract | 400 | 9.91 ± 1.72 | 35 |
|  | 200 | 10.79 ± 1.05 | 29 |
| Mixed herbal extract of *Trachelospermi caulis* and *Pyrola japonica* | 400 (1.0 wt % of arctiin content) | 6.74 ± 0.98 | 56 |
|  | 200 (1.0 wt % of arctiin content) | 7.39 ± 1.24 | 51 |
|  | 20 (1.0 wt % of arctiin content) | 11.44 ± 0.46 | 23 |
|  | 2 (1.0 wt % of arctiin content) | 12.86 ± 0.91 | 15 |

As shown in the above Tables 3 and 4, the mixed herbal extract of the present invention showed an excellent inhibitory effect against the arachidonic acid-induced ear edema. In particular, the highest edema inhibiting rates of 64% and 56%, respectively, were observed when the concentration of the herbal extract used was 400 mg/kg.

EXAMPLE 3

λ Carrageenan-Induced Rats Ear Edema Assay

Figure 1:
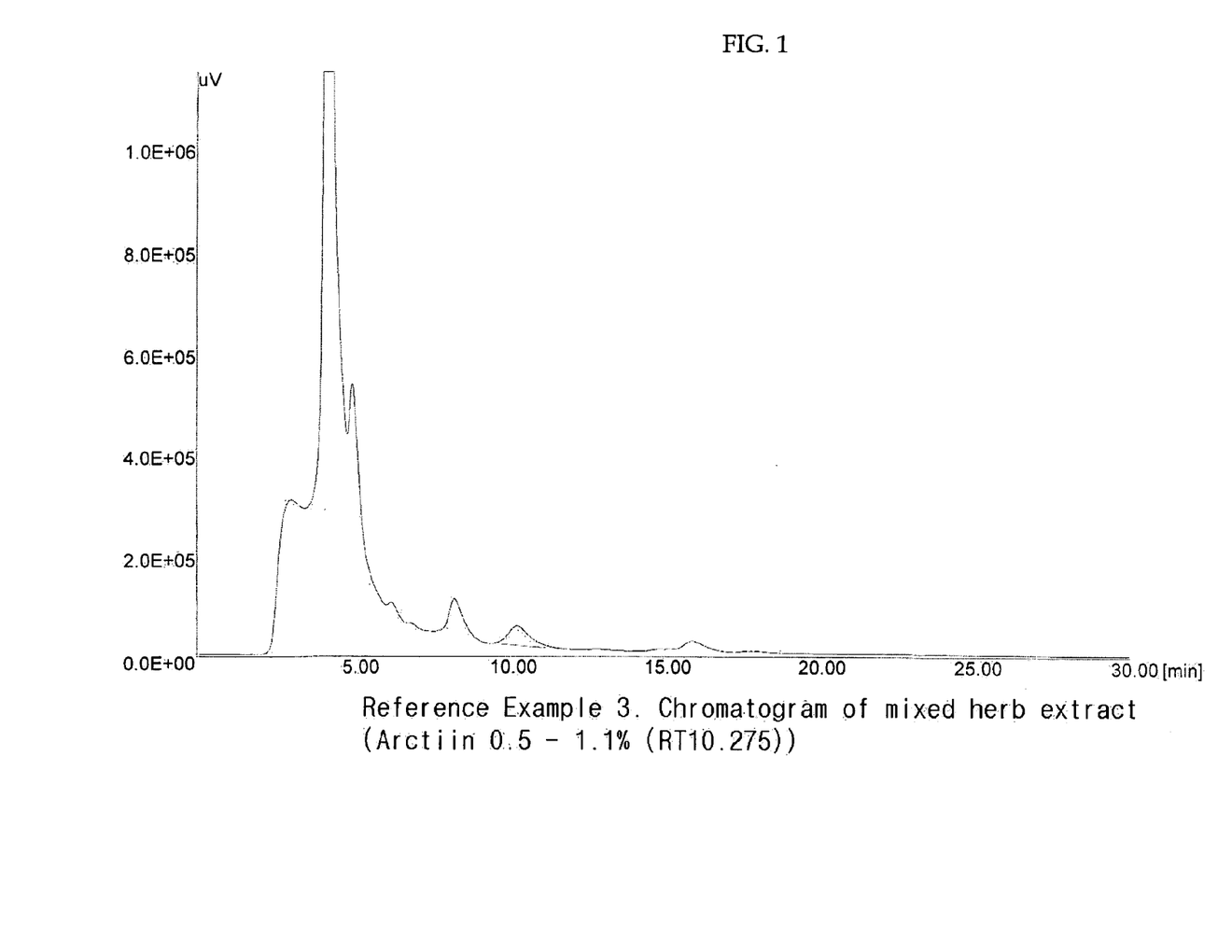
FIG. 1 is an HPLC chromatogram of a mixed herbal extract prepared according to an embodiment of the present invention.
Figure 2:
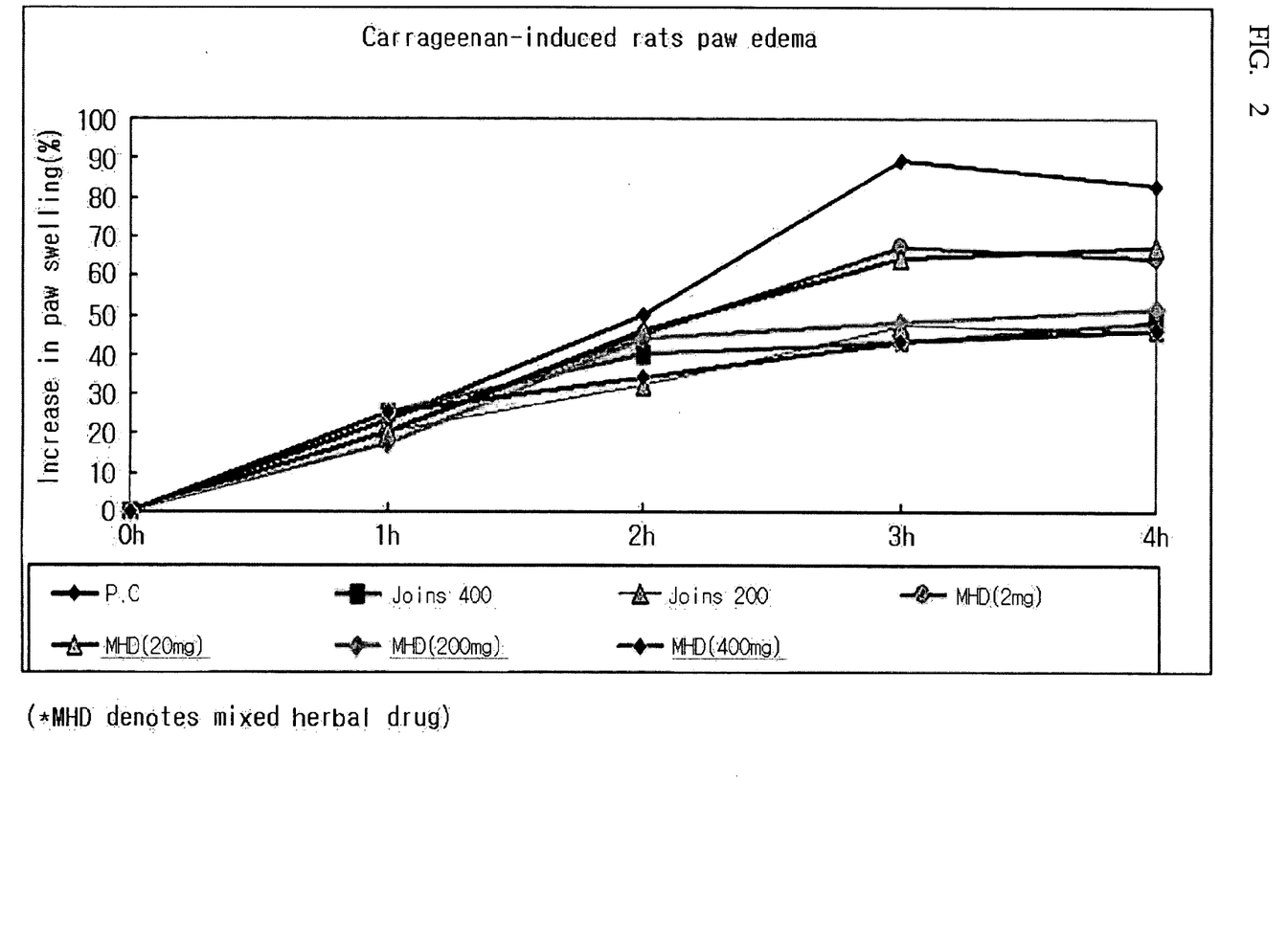
FIG. 2 is a graph showing a comparative data on the increase rate of paw edema induced by carageenan of the present invention.

The effect of the mixed herbal extract obtained in the above reference example 3 on acute arthritis was investigated. The result is shown in the following Table 5 and FIG. 2.

[Test Method]

SD rats with body weight of about 200 g were orally administered with Joins® (SK Pharma Co., Ltd., Korea) at a concentration of 400 mg/kg, *Trachelospermi caulis* extract at a concentration of 200 mg/kg and 400 mg/kg, respectively, *Pyrola japonica* extract at a concentration of 20 mg/kg and 400 mg/kg, respectively, and a mixed herbal extract of *Trachelospermi caulis* and *Pyrola japonica* at a concentration of 2 mg/kg, 20 mg/kg, 200 mg/kg, and 400 mg/kg, respectively. Then, the rats were induced paw edema by injecting 100 μL of 1% carageenan physiological saline solution on the left paw. The paw edema was analyzed by measuring the paw volume in four hours by using plethysmometer, Ugo Basile 7140 (N=7).

TABLE 5

| Treatment | Inflammation Inducing Rate ± S.D. (%) |
|---|---|
| Negative Control | 89 ± 1.67 |
| Positive Control (SK-Joins ®) 400 mg/kg | 43 ± 3.9 |
| *Trachelospermi caulis* (200 mg/kg) | 49 ± 2.92 |
| *Trachelospermi caulis* (400 mg/kg) | 45 ± 4.31 |
| *Pyrola japonica* (200 mg/kg) | 49 ± 4.82 |
| *Pyrola japonica* (400 mg/kg) | 44 ± 3.68 |
| Mixed herbal extract of *Pyrola japonica* and *Pyrola japonica* (200 mg/kg- 1.0 wt % of arctiin content) | 48 ± 1.64 |
| Mixed herbal extract of *Pyrola japonica* and *Pyrola japonica* (400 mg/kg - 1.0 wt % of arctiin content) | 43 ± 2.1 |

1. Data represent the mean of difference in paw edema (mL) ± S.T.D. (n = 12)
2. Neg. Control: Experimental group not induced with edema As shown in the above Tables 5 and FIG. 2, the mixed herbal extract of the present invention showed an excellent therapeutic effect on the acute arthritis. In particular, the highest therapeutic effect was observed when the concentration of the mixed herbal extract used was 400 mg/kg.

EXAMPLE 4

FCA-Induced Arthritis in Rats

Figure 3:
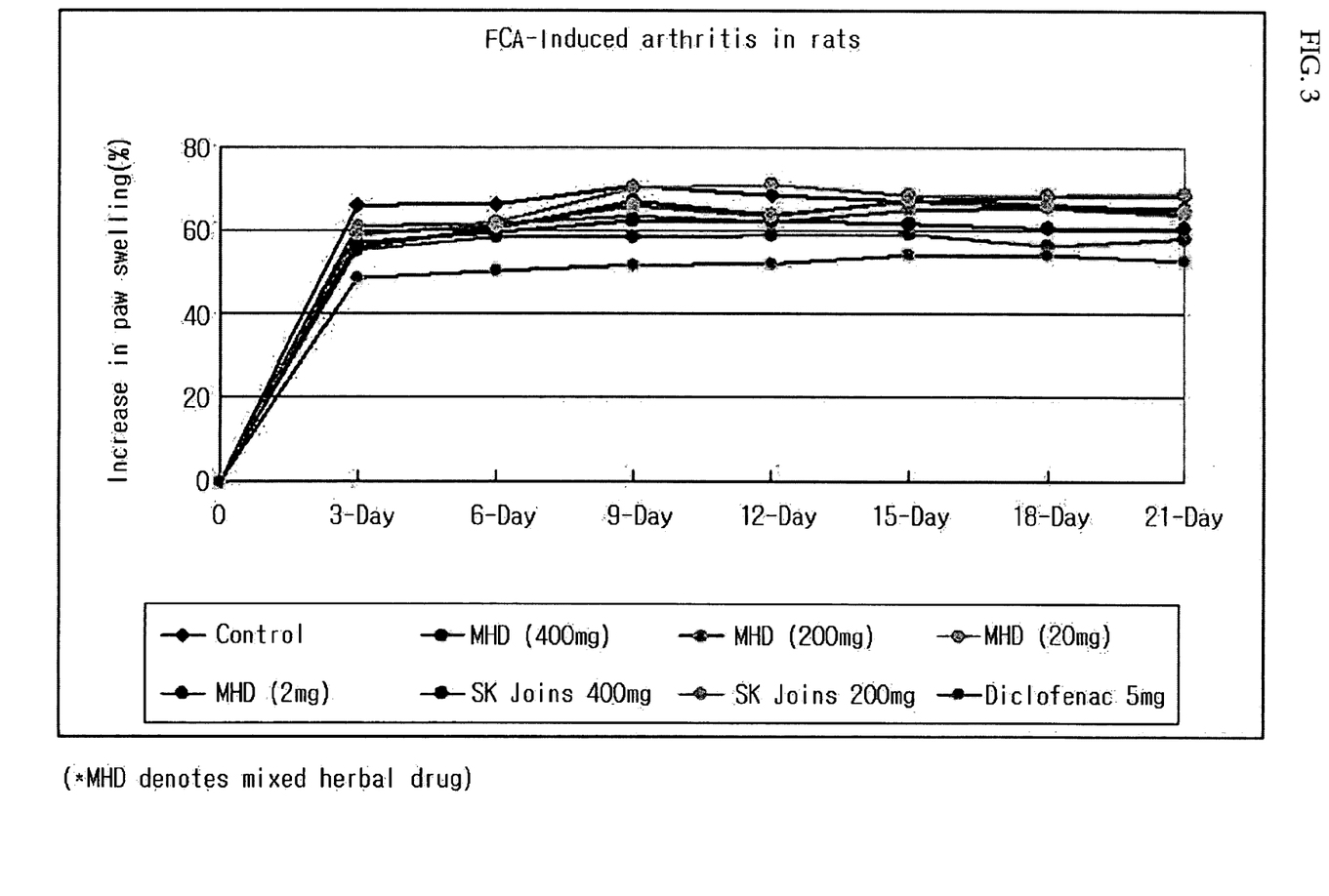
FIG. 3 is a graph showing a comparative data on the increase rate of chronic inflammations induced by FCA of the present invention.

The effect of the mixed herbal extract obtained in the above reference example 3 on chronic arthritis was investigated. The result is shown in the following FIG. 3.

[Test Method]

Seven week old SD rats were separated into each experimental group, and their body weights were measured to calculate the dosage for oral administration. Then, 0.1 mL/paw (Sigma Co., Ltd.) of Complete Freund's adjuvant reagent containing 1 mg/mL of *Mycobacterium tuberculosis* was administered on the center of a paw of hind leg using a 29G syringe. After administration of an adjuvant, test material was orally administered once daily during the same time zone for a period of 21 days, and the level of paw edema was measured once every three days using a plethysmometer (Ugo Basile, Italy), and then calculated the edema increase rate as in the case with paw edema method induced by carrageenan and compared with that of control group. As a substance for positive control, 5 mg/kg of diclofenac was used.

EXAMPLE 5

Acetic Acid-Induced Vascular Permeability in Mice

The inhibitory effect of the mixed herbal extract obtained in the above reference example 3 against vascular permeability was investigated. The result is shown in the following Table 6.

[Test Method]

Seven week old ICR mice were separated into each experimental group, orally administered with *Trachelospermi caulis* extract at a concentration of 20 mg/kg and 200 mg/kg, respectively, *Pyrola japonica* extract at a concentration of 20 mg/kg and 200 mg/kg, respectively, and a mixed herbal extract of *Trachelospermi caulis* and *Pyrola japonica* at a concentration of 2 mg/kg, 20 mg/kg, and 200 mg/kg b.wt., respectively, after dissolving them in distilled water to a concentration of 0.1 mL/10 g b.wt., by using a sonde.

The dosage volume was determined based on the body weight measured on the day of experiment and the control group was only administered with distilled water, a preparation solvent, at a concentration of 0.1 mL/10 g b.wt. Phenylbutazone was orally administered with a dosage of 50 mg/kg b.wt. after suspending it in 0.5% methyl cellulose.

ICR male mice, which were fasted for 12 hours prior to the experiment, were administered with a test substance according to the method of Whittle (1964). Thirty minutes after the oral administration, 2.5% Evans blue solution (0.1 mL/10 g b.wt.) was administered to the caudal vein. Twenty minutes after the administration with Evan's blue solution, acetic acid dissolved in 0.6% of physiological saline was intraperitoneally administered at a concentration of 0.1 mL/10 g b.wt. and induced the accentuation of vascular permeability. Twenty minutes after the administration with acetic acid, each mouse was sacrificed via cervical dislocation, added with 5 mL of a physiological saline solution in abdominal cavity, was slightly shaken. The washing solution was collected from the abdominal cavity and then centrifuged at 2,000 rpm for 10 minutes and the supernatant was measured of its optical density at 630 nm by using a spectrophotometer to calculate the amount of Evan's blue solution flowed into the abdominal cavity. Phenylbutazone (50 mg/kg b.wt.) and indomethacin (1 mg/kg b.wt.) were used as positive control groups.

TABLE 6

| Treatment | No. of Experimental animals | Dosage (mg/kg) | Leakage of dye (μg/10 g b. wt.) |
| --- | --- | --- | --- |
| Negative Control | 11 | 0 | 64.2 ± 3.31 |
| *Trachelospermi caulis* extract | 9 | 20 | 64.12 ± 4.12 |
|  | 9 | 200 | 44.4 ± 4.04** |
| *Pyrola japonica* extract | 9 | 20 | 62.04 ± 3.3 |
|  | 9 | 200 | 53.5 ± 4.31** |
| Mixed herbal extract of *Pyrola japonica* and *Pyrola japonica* | 7 | 2 (1.0 wt % of arctiin content) | 45.5 ± 5.41** |
|  | 7 | 20 (1.0 wt % of arctiin content) | 35.6 ± 4.93** |
|  | 8 | 200 (1.0 wt % of arctiin content) | 24.7 ± 1.58**,#,+ |
| phenylbutazone | 11 | 50 | 39.0 ± 3.45** |
| indomethacin | 14 | 1 | 36.3 ± 2.67** |

**Significantly different (P < 0.05, P < 0.01) from control group
Significantly different (P < 0.05, P < 0.01) from phenylbutazone group
+,++Significantly different (P < 0.05, P < 0.01) from indomethacin group As shown in the above Table 6, the mixed herbal extract of the present invention showed an excellent inhibitory activity against other control groups as compared to that of control group. In particular, the highest inhibitory effect against vascular permeability induced by acetic acid in a dosage-dependent manner, was observed when the concentration of the mixed herbal extract used was 200 mg/kg. Further, when the concentration of the mixed herbal extract used was 200 mg/kg, it showed excellent inhibitory effect against vascular permeability induced by acetic acid was observed as compared to those of positive controls such as phenylbutazone and indomethacin.

EXAMPLE 6

Acetic Acid-Induced Writhing Response in Mice

The pain-relieving effect of the mixed herbal extract obtained in the above reference example 3 was investigated. The result is shown in the following Table 7.

[Test Method]

Seven week old ICR mice were separated into each experimental group, orally administered with Joins® (SK Pharma Co., Ltd., Korea) at a concentration of 400 mg/kg and 200 mg/kg, *Trachelospermi caulis* extract at a concentration of 400 mg/kg and 200 mg/kg, respectively, *Pyrola japonica* extract at a concentration of 400 mg/kg and 200 mg/kg, respectively, and a mixed herbal extract of *Trachelospermi caulis* and *Pyrola japonica* at a concentration of 400 mg/kg, 200 mg/kg, 20 mg/kg, and 2 mg/kg, respectively. One hour after the oral administration, each mouse was intraperitoneally administered with 0.7% acetic acid (0.1 mL/10 g). Ten minutes after the intraperitoneal administration, each mouse was observed by means of stretching (writhing: fully stretching the back or the hind legs) and the result was used as algesia index.

TABLE 7

| Category | Dosage (mg/kg) | No. of writhing (Mean ± S.D.) | Inhibitory rate (%) |
| --- | --- | --- | --- |
| Negative Control (saline solution) | 400 | 34.6 ± 1.6 | — |
| Positive Control (SK-Joins ®) | 400 | 17.5 ± 1.92 | 49 |
|  | 200 | 19.8 ± 1.46 | 43 |
| *Trachelospermi caulis* extract | 400 | 18.8 ± 1.58 | 46 |
|  | 200 | 20.5 ± 1.3 | 41 |

TABLE 7-continued

| Category | Dosage (mg/kg) | No. of writhing (Mean ± S.D.) | Inhibitory rate (%) |
|---|---|---|---|
| Pyrola japonica extract | 400 | 18 ± 0.75 | 48 |
| | 200 | 19.3 ± 0.88 | 44 |
| Mixed herbal extract of Trachelospermi caulis and Pyrola japonica | 400 (1.0 wt % of arctiin content) | 15.8 ± 0.53 | 55 |
| | 200 (1.0 wt % of arctiin content) | 20.4 ± 1.03 | 41 |
| | 20 (1.0 wt % of arctiin content) | 29 ± 0.73 | 16 |
| | 2 (1.0 wt % of arctiin content) | 31.1 ± 0.833 | 10 |

As shown in the above Table 7, the mixed herbal extract of the present invention showed a smaller number of writhing as compared to that of control group. In particular, the highest analgesic effect was observed when the concentration of the mixed herbal extract used was 400 mg/kg.

EXAMPLE 7

Effects of Mixed Herbal Drug on Production of NO, iNOS and TNF-α

The effects of the mixed herbal extract obtained in the above reference example 3 on therapeutic effect on the treatment of factors associated with inflammation were investigated.

[Test Method]

Raw 264.7 cell line, a macrophage derived from a mouse, was treated with LPS (1 μg/mL). 24 hours after the treatment, the culture medium was collected, analyzed via enzyme method and radical chromatography, treated with LPS. Four hours after, the cells were lysed, and then the effects of the combined herbal extract of Trachelospermi caulis and Pyrola japonica on the expression level of nitric oxide (NO), an intrinsic inflammation inducing molecule, inducible nitric oxide synthase (iNOS) and TNF-α, by means of Western blotting using iNOS antibodies.

As for NO, 100 μL of the 24 hour culture medium was collected and then mixed with 100 μL of Griess solution and its optical density was measured at OD 540 nm.

As for iNOS and TNF-α, Raw 264.7 cell line was treated with LPS (1 μg/mL), 4 hours after the treatment, the cells of the resultant were lysed and the whole lysed proteins were collected. The proteins were then separated by electrophoresis and then transferred to a nylon membrane by Western blot, and the amounts of the proteins were analyzed by using iNOS and TNF-α antibodies.

Figure 4:
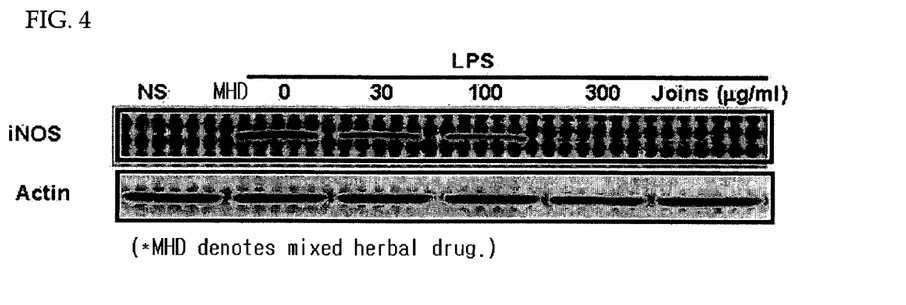
FIG. 4 shows the result of bands obtained from Western Blot using iNOS prepared according to an embodiment of the present invention.
Figure 5:
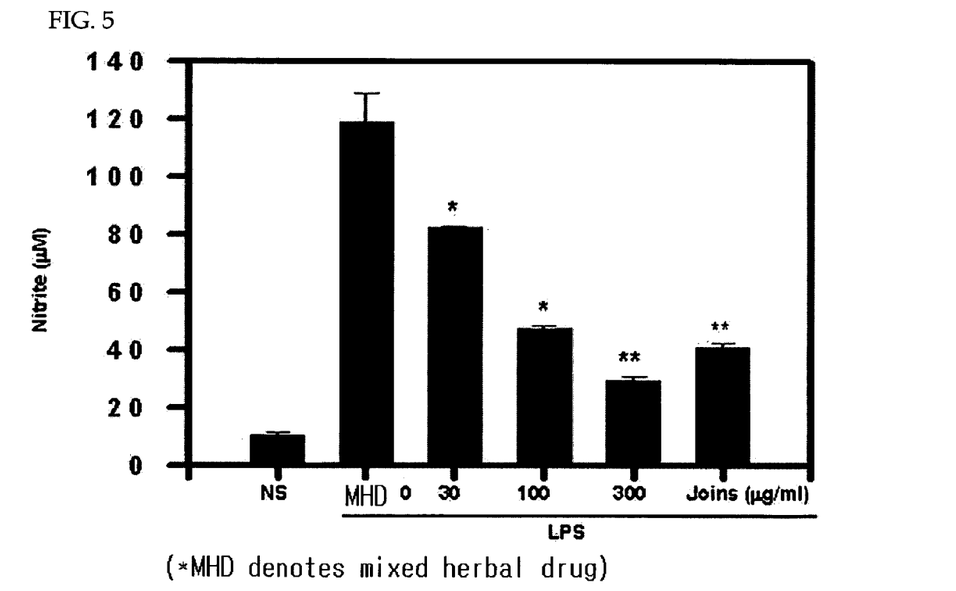
FIG. 5 shows the decrease in the level of NO expression of the macrophage by LPS of the present invention.
Figure 6:
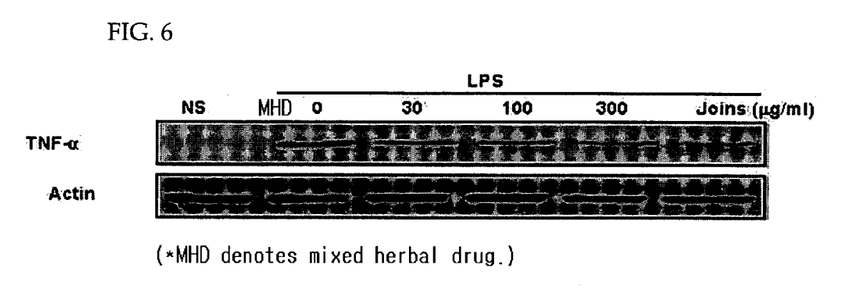
FIG. 6 shows the result of bands obtained from Western Blot using TNF-α antibodies prepared according to an embodiment of the present invention.

FIG. 4 shows the inhibition of the expression level of iNOS; FIG. 5 shows the inhibition of NO production in macrophages by LPS; and FIG. 6 shows the inhibition of expression of TNF-α, thus showing the superior anti-inflammatory effects of the combined herbal extract of the present invention.

EXAMPLE 8

Toxicity Test

The toxicity of the mixed herbal extract of Trachelospermi caulis and Pyrola japonica obtained in the above reference example 3 by repeated administration of 1 g was investigated by using 16 hour fasted 4-5 week old ICR mice (5 mice per group). One gram of the above herbal extract dissolved in 0.5% carboxy methyl cellulose (CMC) was orally administered for 5 days. The result showed that all mice survived and no abnormal lesions in organs were observed.

PREPARATION EXAMPLE 1

Manufacture of Tablets

Tablets for oral administration with the composition as set forth below comprising the mixed herbal extract of the present invention were manufactured by using wet granulation or dry granulation methods.

| [Composition] | |
|---|---|
| mixed herbal extract of Trachelospermi caulis and Pyrola japonica | 200 mg |
| light anhydrous silicic acid | 10 mg |
| magnesium stearate | 2 mg |
| microcrystalline cellulose | 50 mg |
| sodium starch glycolate | 25 mg |
| lactose | 101 mg |
| povidone | 12 mg |
| anhydrous ethanol | adequate |

PREPARATION EXAMPLE 2

Manufacture of Ointments

Ointments with the composition as set forth below comprising the mixed herbal extract of the present invention were manufactured.

| [Composition] | |
|---|---|
| mixed herbal extract of Trachelospermi caulis and Pyrola japonica | 5 g |
| cetyl palmitate | 20 g |
| cetanol | 40 g |
| stearyl alcohol | 40 g |
| isopropyl myristate | 80 g |
| sorbitan monostearate | 20 g |
| polysolvate | 60 g |
| propyl p-oxybenzoate | 1 g |
| methyl p-oxybenzoate | 1 g |
| phosphate and purified water | adequate |

PREPARATION EXAMPLE 3

Manufacture of Injections

Injections with the composition as set forth below comprising the mixed herbal extract of the present invention were manufactured.

| [Composition] | |
|---|---|
| mixed herbal extract of Trachelospermi caulis and Pyrola japonica | 100 mg |
| mannitol | 180 mg |
| sodium phosphate dibasic | 25 mg |
| injectional sterile water | 2,974 mg |

PREPARATION EXAMPLE 4

Manufacture of Transdermal Agents

Transdermal agents with the composition as set forth below comprising the mixed herbal extract of the present invention were manufactured.

| [Composition] | |
|---|---|
| mixed herbal extract of *Trachelospermi caulis* and *Pyrola japonica* | 0.4 g |
| poly acrylate | 1.3 g |
| glycerin | 3.6 g |
| aluminum hydroxide | 0.004 g |
| methyl parabene | 0.2 g |
| acrylic adhesive solution | 14 mL |

As described above, the combined herbal extract of *Trachelospermi caulis* and *Pyrola japonica* of the present invention exhibits excellent inhibitory effects in treating pains, acute inflammation, chronic inflammation and acute edema, vascular permeability and factors associated with inflammation, thus by adjusting the components and their respective amounts effective in the prevention and treatment of inflammatory diseases the standardization of the combined herbal extract of *Trachelospermi caulis* and *Pyrola japonica* can be attained.

Further, in the combined herbal extract of *Trachelospermi caulis* and *Pyrola japonica* of the present invention, where arctiin is indicated as a biomarker, it is possible to manufacture a therapeutic agent for the prevention and treatment and of inflammatory diseases by adjusting the amount of the biomarker.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A pharmaceutical composition comprising mixed extracts of *Trachelospermi caulis* and *Pyrola japonica* for treatment of arthritis and edema, wherein the ratio of mixed extracts from *Trachelospermi caulis* and *Pyrola japonica* is 1:1 to 1:15 by weight.

2. The pharmaceutical composition according to claim 1, wherein the treatment further provides an analgesic effect.

3. The pharmaceutical composition according to claim 1, wherein the composition comprises arctiin in an amount from 0.8 to 1.0 wt. % of the composition.

4. The pharmaceutical composition according to claim 2, wherein the composition comprises arctiin in an amount from 0.8 to 1.0 wt. % of the composition.

5. A method for preparing mixed extracts of *Trachelospermi caulis* and *Pyrola japonica* comprising:
   (a) mixing *Trachelospermi caulis* and *Pyrola japonica*, and performing extraction by using a solvent selected from water, alcohol and an aqueous alcohol solution, and filtering the mixed extracts of *Trachelospermi caulis* and *Pyrola japonica* to obtain a filtrate; and
   (b) concentrating the filtrate to obtain a soluble solid, wherein the ratio of mixed extracts from *Trachelospermi caulis* and *Pyrola japonica* is 1:1 to 1:15 by weight.

6. The method according to claim 5, wherein the extraction is performed by using a solvent with 5-8 times of the weight of the mixed extracts.

7. The method according to claim 5, wherein concentration is performed under reduced pressure.

8. The method according to claim 5, which further comprises:
   (a) suspending the concentrate in an alcohol and centrifuging the suspension to filter;
   (b) reconcentrating the filtrate under reduced pressure; and
   (c) drying, pulverizing and sterilizing the concentrate.

* * * * *